US011776690B2

(12) United States Patent
Roberts et al.

(10) Patent No.: US 11,776,690 B2
(45) Date of Patent: *Oct. 3, 2023

(54) FORECASTING UTERINE ACTIVITY

(71) Applicant: CERNER INNOVATION, INC., Kansas City, KS (US)

(72) Inventors: Andrew Roberts, Overland Park, KS (US); Sasanka Are, Kansas City, MO (US); Jeffrey W. Wall, Overland Park, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 1118 days.

This patent is subject to a terminal disclaimer.

(21) Appl. No.: 16/154,495

(22) Filed: Oct. 8, 2018

(65) Prior Publication Data
US 2019/0139646 A1    May 9, 2019

Related U.S. Application Data

(60) Provisional application No. 62/569,550, filed on Oct. 8, 2017.

(51) Int. Cl.
| | |
|---|---|
| *A61B 5/00* | (2006.01) |
| *A61B 5/11* | (2006.01) |
| *G06N 20/20* | (2019.01) |
| *G16H 50/20* | (2018.01) |
| *G06N 3/08* | (2023.01) |

(Continued)

(52) U.S. Cl.
CPC ............ *G16H 50/20* (2018.01); *A61B 5/1107* (2013.01); *A61B 5/4356* (2013.01); *A61B 5/7267* (2013.01); *A61B 5/7275* (2013.01); *G06N 3/08* (2013.01); *G06N 20/20* (2019.01);
(Continued)

(58) Field of Classification Search
CPC ... A61B 5/4356; A61B 5/7267; A61B 5/7275; G06N 20/20; G16H 50/20
See application file for complete search history.

(56) References Cited

U.S. PATENT DOCUMENTS

| | | | |
|---|---|---|---|
| 11,045,148 B2 * | 6/2021 | Roberts | A61B 5/7275 |
| 2002/0193670 A1 * | 12/2002 | Garfield | A61B 5/344 600/304 |

(Continued)

OTHER PUBLICATIONS

Abry et al., "Hurst Exponent IntraPartum Fetal Heart Rate: Impact of Decelerations", Proceedings of the IEEE Symposium on Computer-Based Medical Systems, Jan. 2013, 7 pages.

(Continued)

*Primary Examiner* — Shirley X Zhang
(74) *Attorney, Agent, or Firm* — Invoke

(57) ABSTRACT

A decision support tool is provided for predicting uterine contractions. The predicted contractions are determined from measurements of uterine activity (UA). The contraction forecast may be made using a plurality of trained predictive models. The forecasts are formed with linear regressive models based, at least in part, on UA data from a reference population. The predicted contractions may be predictions of contraction duration, contraction peak, and time between contractions. In this way, these predicted contractions may be used for decision support for care plans during labor, such as increased monitoring and/or modifying the care plan.

22 Claims, 14 Drawing Sheets

(51) Int. Cl.
  *G16H 20/00*  (2018.01)
  *G16H 40/00*  (2018.01)
  *G16H 50/50*  (2018.01)
(52) U.S. Cl.
  CPC ............. *G16H 20/00* (2018.01); *G16H 40/00* (2018.01); *G16H 50/50* (2018.01)

(56) References Cited

U.S. PATENT DOCUMENTS

| | | | |
|---|---|---|---|
| 2004/0133115 A1* | 7/2004 | Hamilton | A61B 5/4362 600/511 |
| 2007/0233203 A1* | 10/2007 | Euliano | A61B 5/4356 607/46 |
| 2009/0299212 A1* | 12/2009 | Principe | A61B 5/391 600/588 |
| 2011/0192398 A1* | 8/2011 | Euliano | A61B 5/033 128/203.14 |
| 2016/0270658 A1* | 9/2016 | Ater | A61B 8/0866 |
| 2017/0224268 A1* | 8/2017 | Altini | A61B 5/6823 |
| 2019/0133536 A1* | 5/2019 | Roberts | G16H 50/30 |
| 2019/0139644 A1* | 5/2019 | Roberts | G06N 3/045 |
| 2019/0274618 A1 | 9/2019 | Evans | |
| 2020/0196958 A1* | 6/2020 | Penders | A61B 5/7425 |
| 2021/0307703 A1* | 10/2021 | Roberts | A61B 5/02405 |

OTHER PUBLICATIONS

Georgoulas et al., "Predicting the Risk of Metabolic Acidosis for Newborns Based on Fetal Heart Rate Signal Classification Using Support Vector Machines", IEEE Transactions on Biomedical Engineering, vol. 53, No. 5, May 2006, pp. 875-884.

Parer, Julian T., "A Framework for Standardized Management of Intrapartum Fetal Heart Rate Patterns", American Journal of Obstetrics and Gynecology, Jul. 2007, pp. 26.e1-26.e6.

Rotariu et al., "Spectral Analysis of Fetal Heart Rate Variability Associated with Fetal Acidosis and Base Deficit Values", 12th International Conference on Development and Application Systems, Suceava, Romania, May 15-17, 2014, pp. 210-213.

Pre-Interview First Office Action received for U.S. Appl. No. 16/154,480, dated Oct. 15, 2020, 4 pages.

Ayres-De-Campos et al., "Prediction of neonatal state by computer analysis of fetal heart rate tracings: the antepartum arm of the SisPorto® multicentre validation study", European Journal of Obsterics & Gynecology and Reproductive Biology, 2005, pp. 52-60.

Non-Final Office Action received for U.S. Appl. No. 16/154,491, dated Jun. 23, 2022, 13 pages.

* cited by examiner

FORECASTING UTERINE ACTIVITY

CROSS-REFERENCE TO RELATED APPLICATIONS

This application claims the benefit of U.S. Provisional Application No 62/569,550 titled "FORECASTING UTERINE ACTIVITY," filed on Oct. 8, 2017, which is hereby expressly incorporated by reference in its entirety.

BACKGROUND

When a patient is in labor, the contractions of the patient's uterus (also referred to as uterine activity) are monitored to determine the progression of labor. A monitoring device may be used to record measurements of uterine activity in real time, and traditionally, either these measurements and/or the patient's experience of the uterine contractions inform the patient and/or care providers of the presence of a contraction. When contractions are measured electronically, a uterine activity monitoring strip is provided with a uterine activity tracing to show the contractions. At best, these strips provide indications of contractions in real time but do not currently provide indicators of future contractions.

SUMMARY

Systems, methods and computer-readable media are provided for predicting uterine contractions in a future time interval based on monitored physiological variables of a patient in labor and, in some instances, for providing a decision support tool to clinicians and caregivers. In particular, a decision support system is provided for determining likely uterine activity (UA) values for a patient in labor as a predictor for future contractions. The future contractions are forecasted from previous UA measurements taken for the patient. Decision-support may be provided based on the progress of labor as shown through the forecasted UA measurements.

Aspects described herein include acquiring measurements for the patient's UA over time. These measurements form a time series that is used with predictive models to predict future contractions. In one aspects, the patient's UA time series is used to train an ensemble of predictive models where each model generates a forecast of UA values for a future time interval. The plurality of forecasts generated by the ensemble may be averaged to provide a primary UA forecast. In another aspect, a plurality of models are trained with data from a reference population. The trained models may then be used with a particular patient's UA measurements during labor to forecast features of the next contraction to occur within a future time interval. In some aspects, there are three models that each predict a different contraction features, such as contraction peak, contraction duration, and time between contractions. The predictions may be done by identifying contractions using a modified peak-over-threshold approach.

The predicted contractions (future UA values) may then be used to initiate a response action, such as initiating a notification and/or recommendation for therapeutic responses. For instance, a recommendation to proceed to a hospital and/or for increase monitoring of the patient in labor may be provided. Accordingly, one aim of embodiments of this disclosure is to improve upon conventional industry practice by deriving accurate predictive capabilities for contraction monitoring to provide more effective treatment and care during labor and delivery.

BRIEF DESCRIPTION OF THE DRAWINGS

The present disclosure is described in detail below with reference to the attached drawing figures, wherein.

DETAILED DESCRIPTION

Figure 1A:
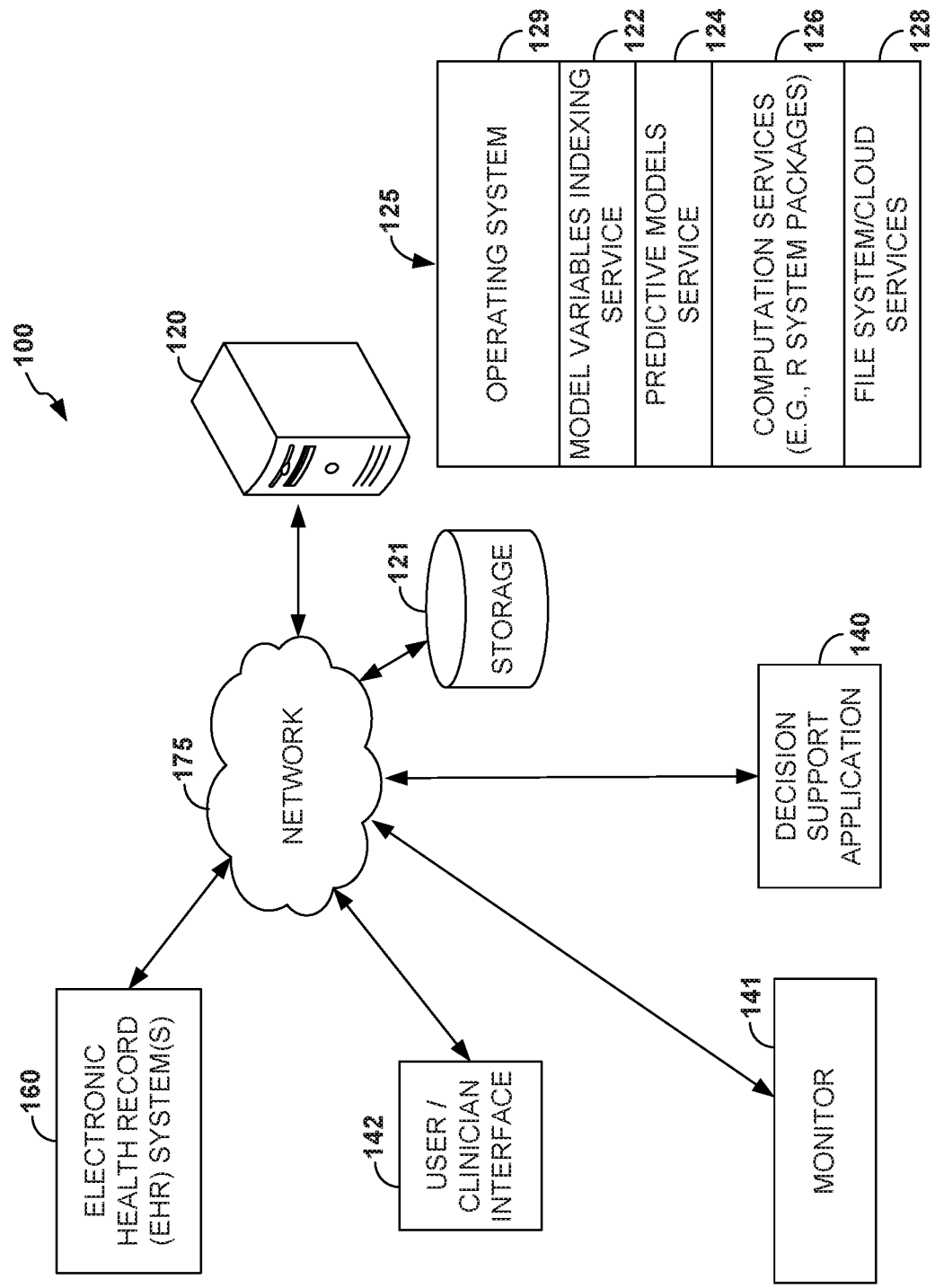
FIGS. 1A and 1B depict aspects of an illustrative operating environment suitable for practicing an embodiment of the disclosure.

The subject matter of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer readable media. Accordingly, the embodiments may take the form of a hardware embodiment, a software embodiment, or an embodiment combining software and hardware. One embodiment takes the form of a computer-program product that includes computer-usable instructions embodied on one or more computer readable media, as discussed further with respect to FIGS. 1A-1B.

Accordingly, at a high level, this disclosure describes, among other things, methods and systems for predicting future contractions for a patient in labor. In some embodiments, the methods and systems may be implemented as a decision support computer application or tool and may be part of a more comprehensive healthcare decision support application for monitoring patients in labor and providing decision support to caregivers. Such decision support technology plays an important part of modern medicine.

Embodiments of the disclosure include systems, methods, and computer-readable media for predicting contractions to occur within a future time interval for a patient in labor. In particular, the decision support system provides forecasts of uterine activity values based on a time series of received UA measurements for a patient. In exemplary aspects, measurements for a patient's UA are acquired during labor, and a UA time series is formed from those measurements. Predictive models are trained to forecast future contractions based on the UA time series.

In some aspects, the contractions are predicted using an ensemble of predictive models, such as an ensemble neural network ARIMA (NNETAR) as described herein. The patient's UA time series may be used to train the plurality of models, and the input and/or parameters of each model may vary to output a plurality of forecasts for future UA values for the patient. In some embodiments, the primary UA forecast is the mean of the forecasts from at least a portion of the ensemble member models. In alternative embodiments, the contractions are predicted using a plurality of predictive models trained on UA measurements from a reference population. The models are trained to predict a feature of a future contraction based on identifying of previous contractions using a peak threshold and a recovery threshold. In some aspects, there are three predictive models that each are trained to predict a particular feature of the next contraction. In exemplary aspects, the predicted features include the magnitude of the next contraction (which may also be referred to herein as the peak UA value), the duration of the next contraction, and the time between contractions.

Based on the forecasted contractions, a response may be initiated. The particular response may depend on comparison of the forecasted UA tracing to reference UA tracings to determine how labor is progressing. For instance, the predictive contractions may be used to determine the stage of labor and whether labor is progressing at an appropriate rate or will be progressing in a safe manner A response based on the forecasts may comprise initiation of a notification of the future contractions, recommendations for modification of a care plan, such as increased monitoring, and scheduling resources relating to a recommended modification of a care plan, and the like. For instance, the future contractions may indicate that labor is not progressing as quickly as desired, thereby prompting a recommendation for intervention, such as medication. Additionally, if a person in labor is monitoring UA at home and the frequency of contractions is expected to increase, a recommendation to see a clinician and/or go to the hospital may be provided.

While uterine activity is routinely monitored during delivery for evidence of existing distress, future uterine activity (i.e., contractions) are not being forecasted to determine the likely progression of labor or to predict future distress. Accordingly, one aim of embodiments of this disclosure is to improve upon conventional industry technology by deriving predictive capabilities for uterine activity to provide more effective treatment and care during labor and delivery. Specifically, these forecasted contractions derived at least in part from physiological measurements of the patient, such as UA measurements, offer an innovative decision support system because it provides an objective manner for determining the progression of labor and identification of likely problems.

Referring now to the drawings in generally and, more specifically, referring to FIG. 1A, an aspect of an operating environment 100 suitable for practicing an embodiment of this disclosure is provided. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of this disclosure. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for forecasting uterine activity at a future time. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, psychiatry/neurology EHR systems. Such EHR systems may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 142) on a computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which labor progression is predicted for a future time according to the embodiments presented herein. Embodiments of user/clinician interface 142 also facilitate accessing and receiving information from a user or healthcare provider about a specific patient or population of patients including patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders for the patient from the clinician/user based on the results of monitoring and predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computing system 120 described below. In an embodiment, decision support application 140 includes a Web-based application or applet (set of applications) usable to provide or manage user services provided by an embodiment of this disclosure. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the technology described herein. In an embodiment, decision support application 140 sends a recommendation or notification (such as an alarm or other indication) directly to user/clinician interface 142 through network 175. In an embodiment, decision support application 140 sends a maintenance indication to user/clinician interface 142. In some embodiments, application 140 includes or is incorporated into a computerized decision support tool, as described herein. Further, some embodiments of application 140 utilize user/clinician interface 142. For instance, in one embodiment of decision support application 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or health care provider about a specific patient or a set of patients, or population according to the embodiments presented herein. Such information may include historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 140 also facilitates receiving orders, staffing scheduling, or queries from a user, based on the results of monitoring and/or forecasted outputs, which may in some embodiments utilize user interface 142. Decision support application 140 may also be used for providing diagnostic services or evaluation of the performance of various embodiments. As shown in example environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment of monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables.

In one embodiment, monitor 141 comprises sensors for obtaining (and, in some instances, pre-processing or interpreting) and recording of maternal vital signs and fetal vital signs, which may be obtained continuously, periodically, or at irregular intervals. For example, in an embodiment, monitor 141 comprises a patient monitoring system for acquiring uterine activity (UA) measurements. In some embodiments, monitor 141 comprises a patient bedside monitor. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about the patient, such as the monitored variables and/or clinical narratives regarding the patient, used according to one embodiment disclosed herein may be received from a patient's historical data in EHR system 160, or from human measurements, human observations, or automatically determined by sensors in proximity to the patient.

Examples of physiological variables monitored by monitor 141 can include vital signs variables, such as heart rate (bradycardia and tachycardia), fetal heart rate (bradycardia and tachycardia), blood pressure, uterine pressure, and respiratory rate, as described herein. Additionally, in some embodiments, monitor 141 may monitor other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient to facilitate clinical decision making In an embodiment, monitor 141 comprises a sensor probe, such as an EEG probe, and a communication link that periodically transmits identification information and probe data to decision support application 140 so that the time series of monitored values is stored on decision support application 140, enabling decision support application 140 to form an alarm indication and/or a physiological variable decision statistic. In an embodiment, decision support application 140 facilitates the collection of raw sensor information, which may be received from monitor 141, and performs signal processing and computations, thereby forming a physiological variable decision statistic, cumulative summing, trending, wavelet processing, thresholding, computational processing of decision statistics, logical processing of decision statistics, pre-processing or signal condition, etc., part or all of which may be performed on monitor 141, decision support application 140, and/or computer system 120.

An embodiment of monitor 141 stores user-derived data locally or communicates data over network 175 to be stored remotely. In an embodiment, decision support application 140, or the computer system on which it is operating, is wirelessly communicatively coupled to monitor 141. Application 140 may also be embodied as a software application or app operating on a user's mobile device, as described above. In an embodiment, decision support application 140 and monitor 141 are functional components of the same device, such as a device comprising a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or the computer system supporting decision support application 140 for performing signal conditioning of the measured patient variable(s). In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for predicting uterine contractions in a future time interval based on physiological variables monitored for a patient in labor as described in connection to method 200 of FIG. 2 and method 600 of FIG. 6.

Computation services 126 perform statistical software operations. In an embodiment, computation services 126 and/or predictive models service 124 may include computer-performed services or routines for utilizing one or more models, including logistic models, for predicting uterine contractions, such as the models described in connection to FIGS. 2-10C. In one embodiment, computation services 126 includes computer-performed services or routines that may be implemented in the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as package forecast, which includes the NNETAR and ARIMA functions described herein for fitting a neural network to a time series. Computation services 126 also may include natural language processing services (not shown) such as Discern nCode™ developed by Cerner Corporation, or similar services. In an embodiment, computation services 126 include the services or routines that may be embodied as one or more software agents or computer software routines.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer-storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
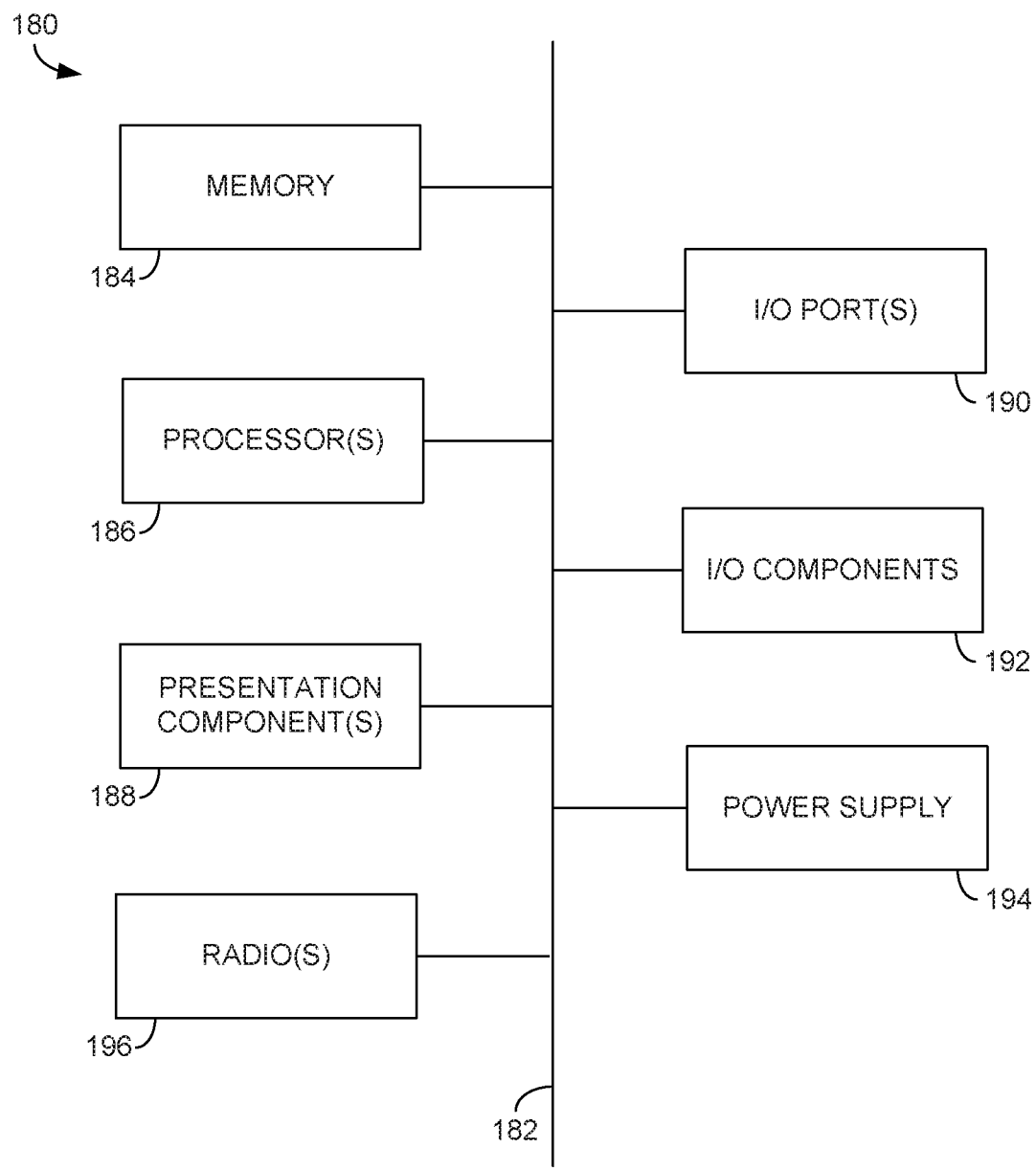

Turning briefly to FIG. 1B, there is shown one example embodiment of computing system 180 representative of a system architecture that is suitable for computer systems such as computer system 120. Computing device 180 includes a bus 182 that directly or indirectly couples the following devices: memory 184, one or more processors 186, one or more presentation components 188, input/output (I/O) ports 190, input/output components 192, radio 196, and an illustrative power supply 194. Bus 182 represents what may be one or more busses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1A is merely illustrative of an exemplary computing system that can be used in connection with one or more embodiments of the present disclosure. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 184 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 184 or I/O components 192. Presentation component(s) 188 present data indications to a user or other device. Exemplary presentation components include a display device, speaker, printing component, vibrating component, etc.

In some embodiments, computing system 196 comprises radio(s) 196 that facilitates communication with a wireless-telecommunications network. Illustrative wireless telecommunications technologies include CDMA, GPRS, TDMA, GSM, and the like. Radio 196 may additionally or alternatively facilitate other types of wireless communications including Wi-Fi, WiMAX, LTE, or other VoIP communications. As can be appreciated, in various embodiments, radio 196 can be configured to support multiple technologies and/or multiple radios can be utilized to support multiple technologies.

I/O ports 190 allow computing system 180 to be logically coupled to other devices, including I/O components 192, some of which may be built in. Illustrative components include a microphone, joystick, game pad, satellite dish, scanner, printer, wireless device, etc. The I/O components 192 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
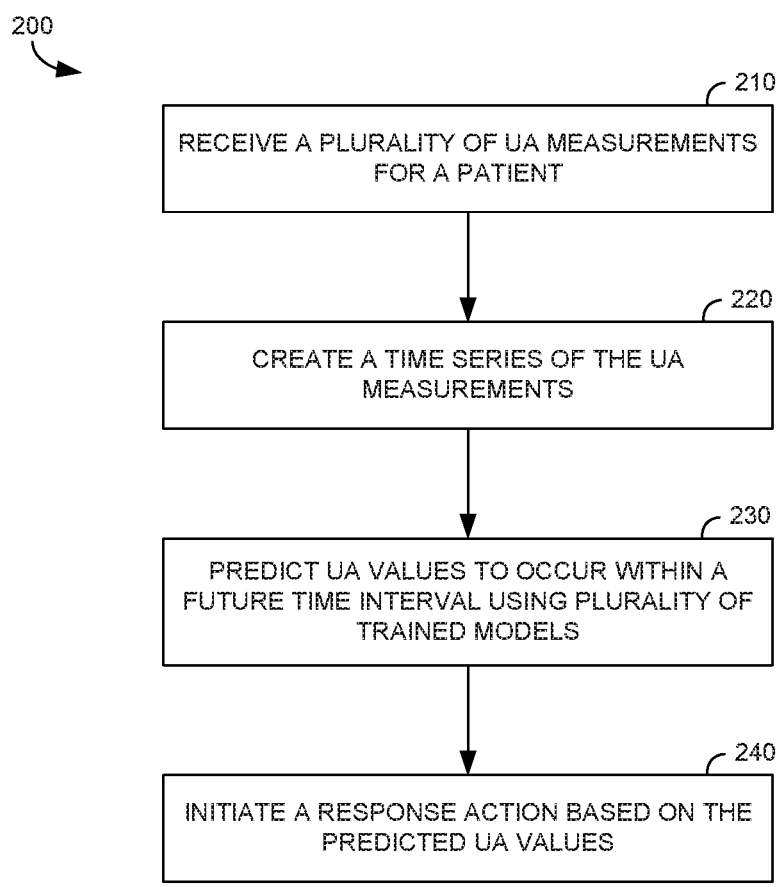
FIG. 2 depicts a flow diagram of a method for predicting uterine activity values using measurements from the patient acquired during labor and suitable for implementation in a decision support system, in accordance with an embodiment of the disclosure.

Turning now to FIG. 2, an example embodiment of a method for predicting uterine contractions at one or more future time intervals is provided and is referred to generally as method 200. In particular, example method 200 utilizes previous UA measurements for predicting contractions to occur in the future. In some embodiments, method 200 is suitable for implementation as a computer-performed decision support tool or application for labor and delivery monitoring and, thus, care plans for proceeding with a delivery based on more objective and accurate indicators of uterine contractions than conventional technology would otherwise allow.

With reference to FIG. 2 and method 200 generally, the method 200 of providing decision support during labor and delivery by predicting uterine contractions at one or more future time intervals is provided. First, at step 210, a plurality of measurements of physiological variables for a patient is received. The plurality of measurements may have been acquired for the patient over a period of time while the patient is in labor. In exemplary aspects, the physiological variables include uterine activity (UA). UA measurements may be recorded using either internal monitoring devices or external monitoring devices. For internal monitoring devices, UA may be measured as uterine pressure (typically measured in units of mmHg), while external monitoring devices may provide indications of UA through skin tension measurements. In exemplary aspects, UA is measured as uterine pressure using an internal monitoring device, which does not require the additional re-calibration based on the maternal patient's body mass index that is often involved when using external monitoring devices. Additionally, in some embodiments, additional physiological variables are monitored and received. For instance, the heart rate (i.e., maternal heart rate), fetal heart rate, the patient's level of dilation, patient's age, and fetal gestational age may be received.

The measurements for the physiological variables may be received from the patient's EHR, such as a medical EHR within EHR system 160 in FIG. 1, or other data storage, or may be received directly from a monitoring device, such as patient monitor 141. Embodiments of step 210 may acquire the physiological variable measurements continuously, periodically, or at non-regular intervals. In some embodiments, the date/time information for each measurement is stored with the measured variable values.

Next, as step 220, a time series is constructed for one or more of the physiological variables measured. The time series may be constructed by appending the most recent physiological variable measurements to the historical measurements using the associated date/time information. In some embodiments, the historical measurements comprise measurements obtained within a recent timeframe such as the previous 20 minutes, previous hour, or previous several hours. In such embodiments, only historical measurements from within this recent timeframe are retrieved and used for the constructing time series. In some aspects, the time series is evaluated to determine whether it is of sufficient length. In one embodiment, where the time series is determined to be greater than or equal to a pre-determined length, method 200 proceeds to step 230. But if the time series is not long enough (i.e., does not meet the pre-determined length), then method 200 returns to step 210, where additional measurements may be acquired. In one embodiment, the pre-determined minimum length comprises 20 minutes, but it is contemplated that other durations may be used for the threshold length.

Figure 3:
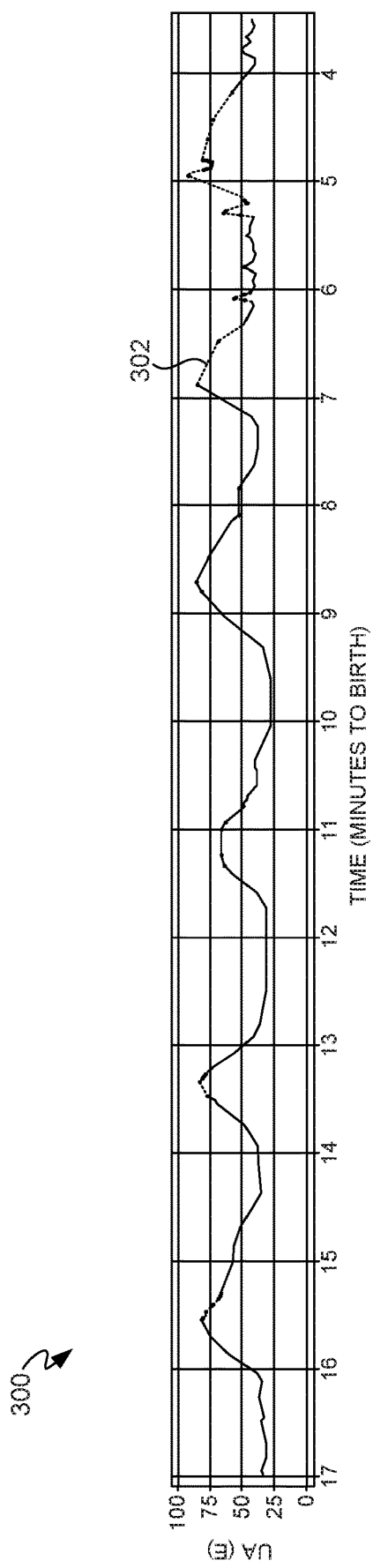
FIG. 3 depicts example UA monitoring strips with data gaps identified in accordance with an embodiment of the disclosure.

In exemplary aspects, forming a time series in method 200 further comprises pre-processing the data to remove artifacts and/or address missing data, as shown in FIG. 3. FIG. 3 illustrates an example UA time series strip 300 based on measurements of the patient. The UA time series strip 300 depicts UA measurements (in mmHg) in time until birth. As illustrated, the example UA time series strip 300 includes missing gaps, such as the gap 302 at approximately 6 minutes and 50 seconds prior to birth. The gaps are displayed as dashed lines in FIG. 3.

Missing data may arise when one or more of the devices (e.g., an internal or external uterine contraction monitoring device) is either not powered on or is powered on but not properly attached to the patient, which results in 0's being recorded. In some embodiments, when there is a gap between observations that is 60 seconds or longer in length, the data is separated into distinct segments to be analyzed separately, and any segment that less than 15 minutes long is removed from the time series. Segments with gaps less than 60 seconds may be retained, and interpolated values for those gaps may be used. For example, FIG. 3 shows dashed lines to account for gaps that are retained in the time series.

In addition to gaps, artifacts in the time series may be detected and removed. Artifacts have non-zero values but are not true observations and may be the result of movement of the monitor or the patient coughing, resulting in a sudden increase or decrease in values. Detected artifacts may be removed, thereby creating additional gaps in the data. Artifacts are often present when there is sudden spikes in the tracing.

Further, in some aspects, processing the data into different segments is based on the type of maternal monitoring devices for each UA data point. In some embodiments, there are three possible indicators for the monitoring device: internal, external, or "NO TRANSDUCER." As previously mentioned, internal monitoring devices record UA in terms of pressure, and, as such, a physical unit (e.g., mmHg) is associated with the observations. External devices typically measure skin tension and do not produce observations associated with a physical unit. External devices typically require calibration each time they are used because readings from external devices may vary between patients (particularly based on a patient's BMI) and may also vary within the same patient encounter if the calibration changes. Because of this, readings from external devices generally only have meaning relative to other observations from the same device with the same calibration. Due to the differences between external and internal maternal monitoring devices, segments of data from different devices may be analyzed separately, and segments of data from external devices when different calibrations may further be analyzed separately. To account for a change of device (or calibration), a segment may be split into two distinct pieces anytime the maternal monitoring device changes for more than 10 seconds. As previously mentioned, in some embodiments, only segments with a duration of at least 20 minutes are retained.

In example embodiments, the Porto system is used to automate the artifact identification and imputation process. In accordance with the Porto system, a change in UA values between any two observations that is greater a threshold change is identified as an artifact, and a linear interpolation is applied between the first of these two observations and the first observation in the next stable stretch. In an embodiment, the threshold change is 10 units (such as 10 mmHg) between any two observations when the UA measurements are recorded with an internal monitoring device. In addition to artifacts occurring in the middle of a tracing, the beginning and end of segments may have artificial observations that may be attributed to the monitoring device recording while it is still being positioned or removed. Accordingly, in some aspects, observations before the first stable segment or after the last stable segment are removed to ensure the data being analyzed is of a sufficient quality. A stable segment for UA data may be one in which there are five consecutive values having differences of less than five units. A portion of the time series may be discarded if the delay between an artifact and the next stable stretch is at least one minute in length.

Additionally, in some aspects, processing the data for the times series also includes imputing data to account for certain sampling delays. For instance, in some aspects, the exemplary sampling rate is a uniform rate of 1 second with no missing data. However, there may be larger gaps between observations caused by the sampling rate of the monitoring devices being set to a different rate due to other uses of the devices and data. Additionally, the sampling rates may be not uniform. To achieve a sampling rate of 1 second, data may be imputed any time there is a delay greater than 1.5 seconds between consecutive samples. In this case, the number of imputed observations is determined to make the sampling rate as close to 1 Hz as possible. The imputed UA values may be determined using Stine interpolation (for example, using the 'pracma' package in R), and noise may be added to the interpolated data. The added noise may be Gaussian with a mean of 0 and a standard deviation equal to the standard deviation of the observation values. Segments of data where no more than 20% of the data was imputed due to artifacts or missing values may be retained to form the time series.

Continuing with FIG. 2, at step 230, method 200 further includes using a plurality of trained models to predict one more UA values within a future time interval. The trained models use the patient's UA time series as input data to predict UA and, specifically, to predict uterine contractions. In example embodiments, the one or more forecasting models include an ensemble neural network ARIMA (NNETAR). The ensemble NNETAR comprises a plurality of NNETAR models. Each NNETAR model may be produced by a machine learning algorithm using a UA time series as input and may forecast future values of UA based on the patient's past UA measurements. When making the forecasts, the past values of UA may be weighted, and each NNETAR model may be trained to determine the optimum coefficient weights to assign to those past values and determine how much data is needed to make predictions. As more data is received, the weighting of functions for a particular model may be adjusted. In contrast with standard ARIMA (autoregressive integrated moving average) models, NNETAR models utilize nonlinear functions of the past values to produce the forecasts. In an example embodiment, the 'nnetar' function from R-system's forecast package is used to produce the models, as described above.

Once trained for the patient, each predictive model uses the most current values to forecast the next value in the time series. The number of known values needed to forecast the next value may be referred to herein as the minimum lag count. In some embodiments, the ensemble members may be trained after at least 15 minutes of received data. In an example embodiment, the model requires the previous 10 values to forecast the next value. For example, values $v_{91}, \ldots, v_{100}$ are used to predict $v_{101}$. To forecast values further out, the model may use an interactive process, using forecasted values to predict other future values. For instance, if the only known values are $v_1, \ldots, v_{100}$, the model uses known values $v_{92}, \ldots, v_{100}$ in conjunction with the predicted value $v_{101}$ to determine $v_{102}$, and so on to forecast values $v_{101}, \ldots, v_{110}$. In some embodiments, the forecasted UA measurement is measured in the same manner as the input. For instance, if the input is uterine pressure measurements acquired from an internal monitor, the forecasted UA is a uterine pressure measurement predicted within a future tine interval. In some embodiments, the future time interval is five minutes, but it is contemplated that other future intervals such as 1 minute, 10 minutes, and 15 minutes, may be used.

As previously stated, there may be a plurality of predictive models, such as NNETAR models, using the UA data from the same patient to predict the patient's future UA values. To obtain a singular UA forecast, the predicted UA values from the ensemble NNETAR models may be averaged. By averaging predictions from different models, a more robust prediction may be provided. Additionally, a mechanism for estimating forecast error may be provided through an ensemble.

In some embodiments, offsets of the time series data may be used for inputting data into the ensemble of models. Offsets may be obtained by using, as input for the model, a time series that is sampled less frequently than a baseline frequency. For instance, in exemplary aspects, the baseline frequency is 1 Hz. To train and update six models, for instance, six different time series may be created from the same UA time series by using offsets rather than training the six models with the same data points. The first data set for a first model may comprise $v_1; v_7; v_{13}, \ldots$; the second data set for a second model may comprise $v_2; v_8; v_{14}, \ldots$; and so on. In this way, the models in the ensemble may be trained with every sixth observation, and the different data sets within the time series may be used as input for different models.

To produce the ensemble, the inputs and parameters that are fed into each model are varied. In some embodiments, the following inputs and parameters vary between the different models: (1) the length of the time series used to train the model, (2) the maximum lag, and (3) the number of offset time series. In some embodiments, the length of training data for a particular model may be one of 5 minutes, 10 minutes, and 15 minutes. The maximum lag is a measure of how much data may be used to make the predictions. In some embodiments, the maximum lag may be over a period of time, such as 18 seconds, 30 seconds, 60 seconds, and/or 120 seconds. The number of offsets is a measure of the number of observations between observations that are used as input. For example, in embodiments in which every sixth observation is used, the offset number is five. Each model may be trained with a different combination of parameters, including length of training data, maximum lag, and number of offsets.

In an example reduced to practice, the models are trained using the following parameters: (1) length of time series is either the last 5 minutes, 10 minutes, or 15 minutes; (2) the maximum lag values is 18 seconds, 30 seconds, 60 seconds or 120 seconds; and (3) the number of offsets is five (such that a particular time series can provide five different data sets). Using all possible combinations of those parameters, 60 different models were trained to forecast UA values. It is contemplated that the number of models in the ensemble may be more or less than 60 depending on the different parameters used. In some embodiments, the number of models is between 40 and 60 models. In some embodiments, there are five different maximum lag values.

As new data comes in, each model may update the weighting of the functions and generate an updated forecast. The models may be updated on a regular basis and, with every update, more data may be received. The models, for example, may be updated every 1 minute or 5 minutes. In addition to updating based on new data, the models may be updated by changing the weights of the different lags. Accordingly, in some embodiments, the functions themselves are updated and, in other embodiments, only the coefficients (the weighting of the functions) are updated. Every update may result in a new forecast be generated.

Using the forecasts from each ensemble member (i.e., each predictive model), an overall, primary prediction may be generated. The primary forecasted UA measurement may be the mean of all the ensemble forecasts. In some embodiments, although each ensemble member uses different coefficient weights, the ensemble members are not weighted when the forecasts are averaged to produce the primary forecast. In alternative embodiments, the ensemble members are weighted differently based on which ensemble members are performing the best to obtain a weighted average as the primary forecast. A determination of the performance of each model may be based on intermediate observations (i.e., observation between model updates) in real time. For example, Kalman filtering may be used for data assimilation to produce the weighting of the ensemble members as well as to calculate an error estimate. In some embodiments, using the intermediate values and error rate, the ensemble members may be better tuned and less accurate members may be weighted less or even eliminated.

In an example embodiment reduced to practice, the ensemble was an NNETAR trained using UA measurements from internal monitoring devices measuring three patients. In this example, the training data came from patients who all had vaginal deliveries, but it is contemplated that the models may be trained using data from labors resulting in vaginal and cesarean section deliveries. The UA measurements were recorded up to ten hours before delivery. In other embodiments, the data may be restricted to being from within three and half hours of delivery to the last 30 minutes to obtain more regular contractions, and for a patient with a first pregnancy, the observation time may be from four to four and a half hours.

Figure 4:
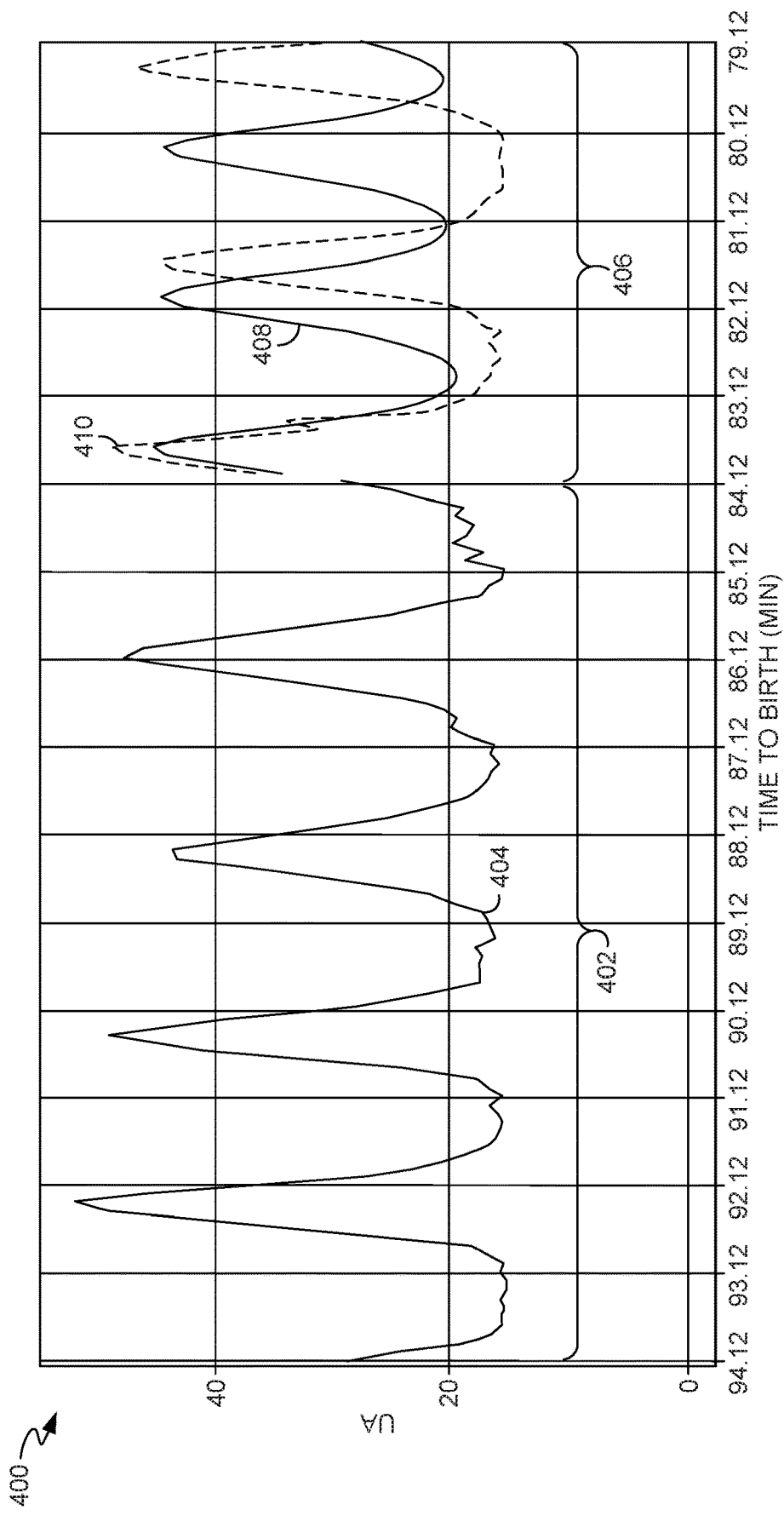
FIG. 4 depicts an example UA monitoring strip with UA values forecasted using one predictive model.
Figure 5A:
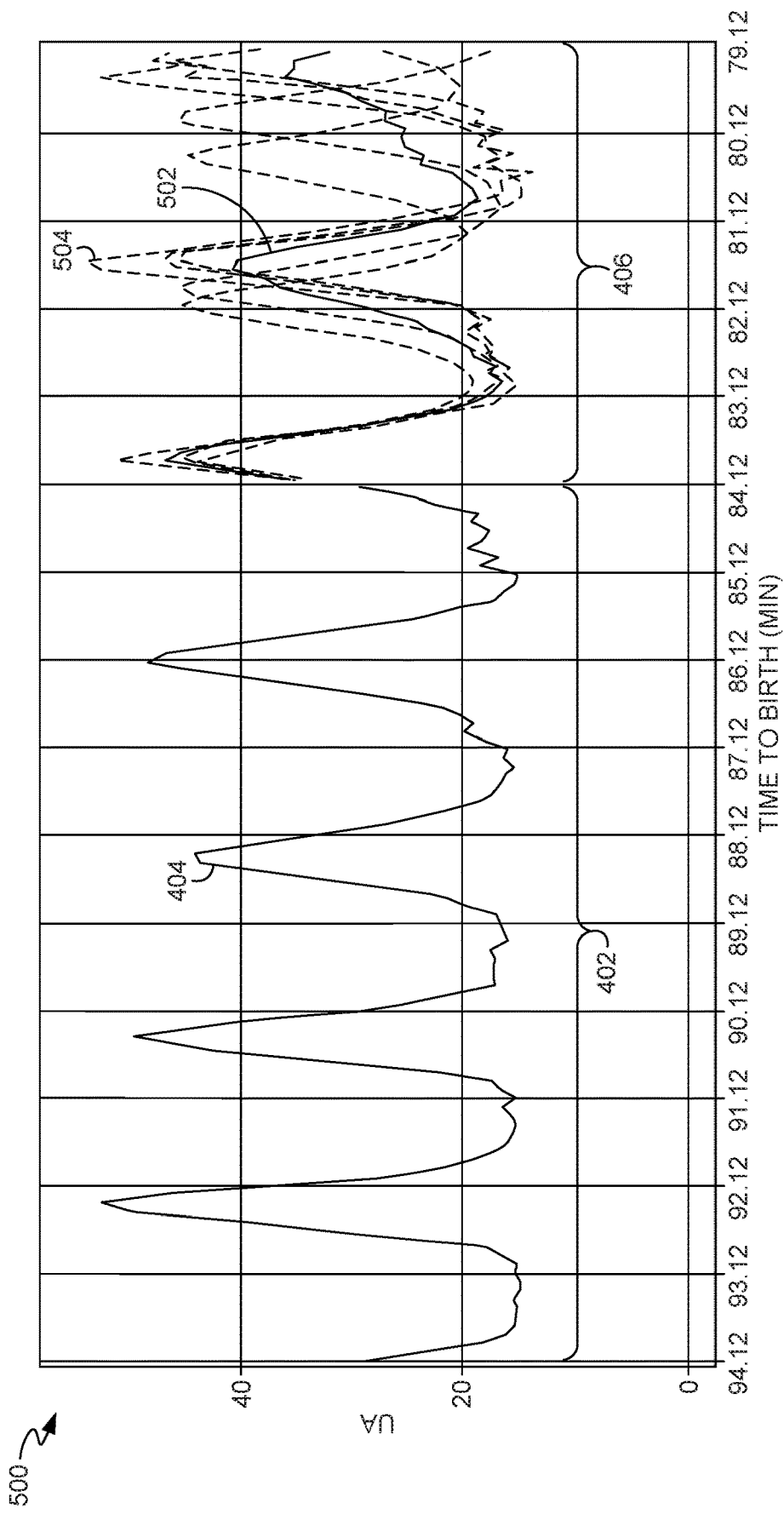
FIGS. 5A-5B depicts an example UA monitoring strip with UA values forecasted the ensemble of predictive models in accordance with an embodiment of the disclosure.
Figure 5B:
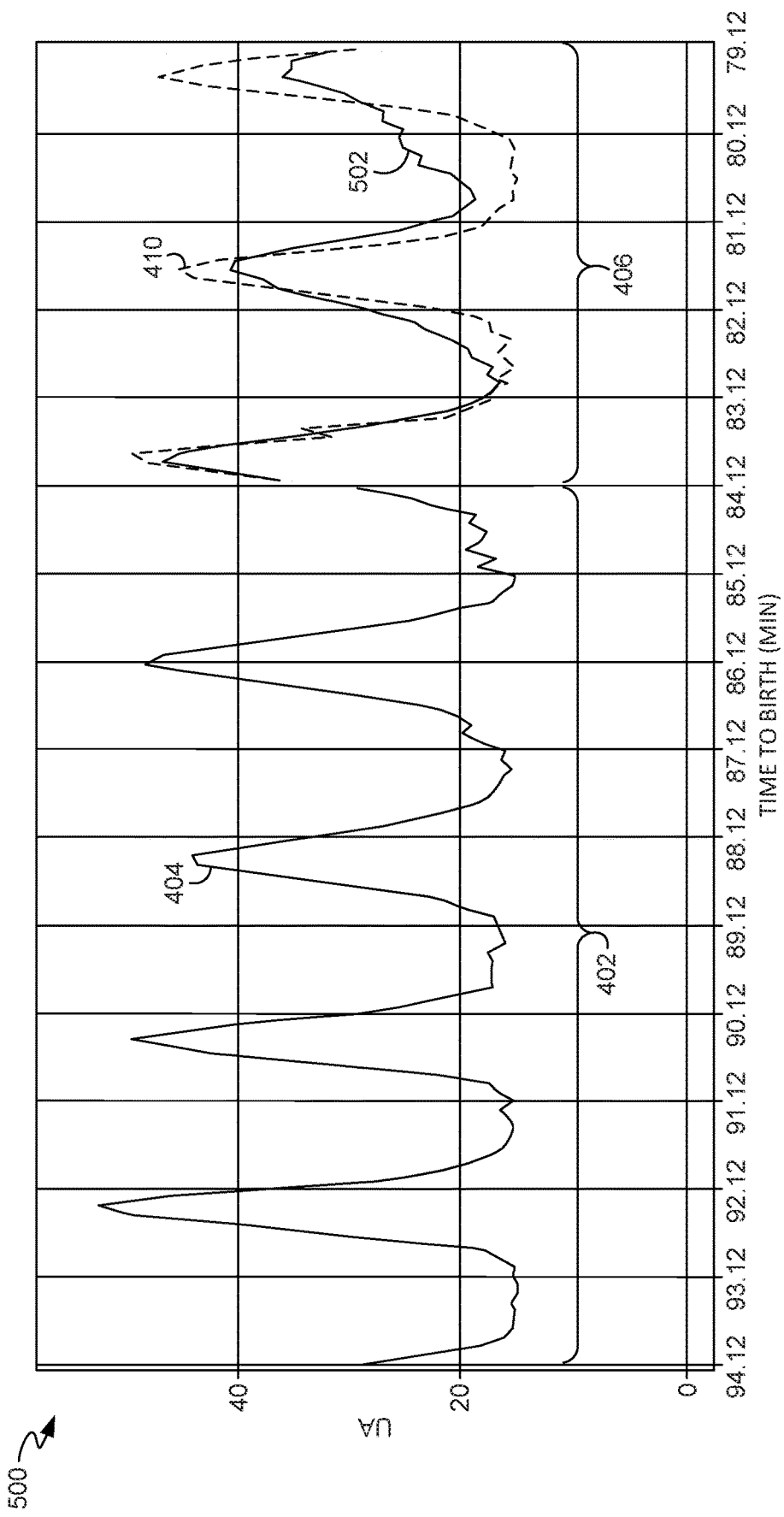

FIGS. 4 and 5A-5B depict example UA monitoring strips that with UA values forecasted using one or more trained models. In FIG. 4, example UA monitory strip 400 depicts a tracing of UA measurements during labor. The UA tracing 404 during time from 402 (94.12 minutes to 84.12 minutes prior to birth) represents actual UA values measured for a patient. Forecasted UA tracing 408 (shown as a solid line) in time period 406 (84.12 minutes to 79.12 minutes prior to birth) represents UA values predicted using a single trained model based on at least some of the UA measurements from UA tracing 404. Actual UA tracing 410 (shown as a dashed line) in time period 406 illustrates the patient's actual UA measurements during that time period. As depicted in FIG. 4, values forecasted from a single model may not provide the most accurate prediction of future contractions.

In contrast, FIG. 5A depicts an example UA monitoring strip 500 that illustrates forecasts of UA measurements from five out of the 60 models. UA monitoring strip 500 illustrates the same UA tracing 404 in time period 402 as depicted in FIG. 4. In time period 406, however, UA monitoring strip 500 includes a plurality of forecasted UA tracings each produced from a model and displayed as a dashed line, such as forecasted UA tracing 504. Primary forecast UA tracing 502 (depicted as a solid line) in time period 406 represents the primary forecast derived from the forecasts of the plurality of models. For instance, the primary forecast in primary forecast UA tracing 502 may be the mean of the plurality of forecasted UA tracings shown in dashed line. FIG. 5B depicts example UA monitoring strip 500 with primary forecast UA tracing 502 illustrated with actual UA tracing 410 (shown in a dashed line) in time period 406. As illustrated, the primary forecast UA tracing 504 generated using an ensemble of models is more accurate (closer to the actual UA tracing 410) than the forecasted UA tracing 408 using a single model in FIG. 4.

As illustrated in FIG. 5, the forecasted contractions (i.e., the output of the ensemble) may comprise a predicted time series where the predicted time series comprises a set of UA measurements for the future time interval. The predicted time series indicates a duration of a future contraction, a height of the peak of the future contraction, and time of the future contraction after the previous contraction. In some embodiments, example UA monitoring strip 500 may be provided on a graphic user interface for presentation to a user, such as a clinician. In some aspects, all or some of the forecasts from the individual models, such as what is shown in FIG. 5A, are displayed on the UA monitoring strip. In other embodiments, only the primary forecast is presented with the actual UA measurements on the monitoring strip as shown in FIG. 5B.

Returning to method 200 of FIG. 2, based on the forecasted contraction(s), a response action may be initiated, as shown at step 240. One such response action may be a recommendation or notification that is emitted or otherwise communication to a caregiver responsible for the patient's care, such as an obstetrician. For instance, when the forecasted contraction indicates a contraction with a peak above a threshold and/or within a threshold duration, a notification of the forecasted contraction may be generated and communicated via a bedside alarm, user/clinician interface (such as interface 142 described in FIG. 1A), or may be communicated to a smartphone or personal computing device of a caregiver. The notification may illustrate the forecasted contraction on a UA monitoring strip and/or may indicate that the next contraction is forecasted to be a strong contraction. Additionally, a stage of labor may be identified using the forecasts, and a notification of the stage of labor may be provided. A notification may also be provided when the contraction is predicted within a future time frame to indicate that a next contraction may be expected within the near future. Additionally, some embodiments of step 240 may comprise storing the result of the forecasted contraction(s) in an EHR associated with the patient and further may include providing the patient's EHR (or facilitating access to the EHR) in the notification.

In addition to or alternatively of the notification, a set of one or more actions relating to therapeutic responses may be initiated. For example, as described herein, the forecasted contraction may indicate that the contractions should be monitored by a care giver, such as an obstetrician, and based on that determination, may recommend monitoring and/or admittance to the hospital. In some embodiments, a determination that the contractions are forecasted within a sufficient frequency may initiate a recommendation for monitoring by a caregiver. For instance, when contractions first begin, the expecting mother may monitor the contractions at home to determine when to go to the hospital for delivery. Additionally, some embodiments recommend actions based on determinations that labor is not progressing in an expected way based on the forecasts. A recommendation may be provided in conjunction with a notification of the forecasted contractions and/or may be provided via a user/clinician interface, such as interface 142, described in connection with FIG. 1A.

Yet another action that may be initiated comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan due to the expected upcoming contractions. A further action that may be initiated comprises scheduling healthcare resources for the patient. For example in one embodiment, it may be determined, based on forecasted contractions, that the patient has reached a threshold contraction duration and/or contraction strength that additional resources, such as staff, may be scheduled to monitor and treat the patient in labor. In one embodiment, this action comprises modifying or updating a resource/scheduling electronic record in a resource/scheduling system.

Figure 6:
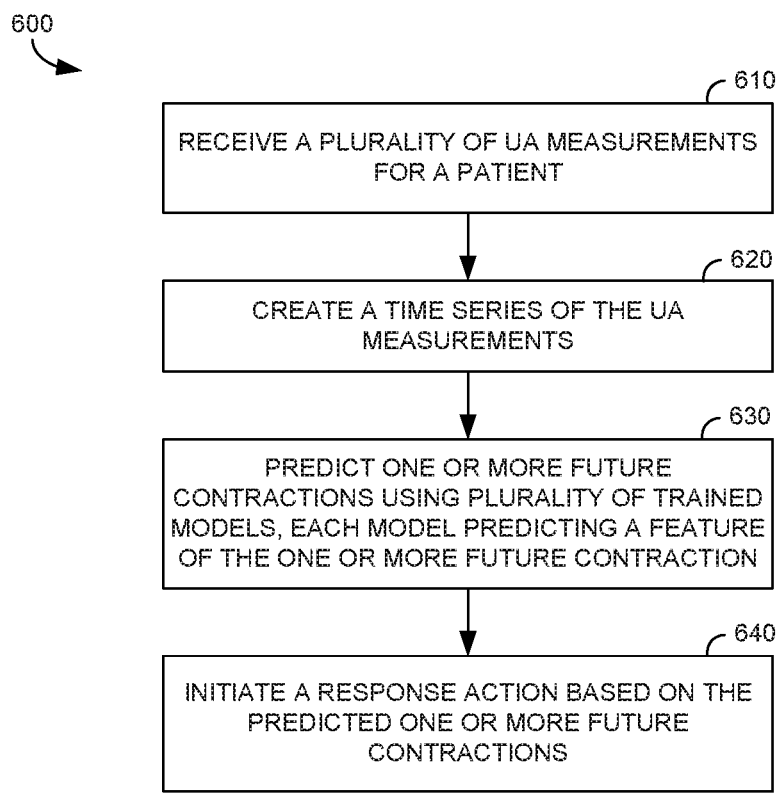
FIG. 6 depicts a flow diagram of a method for predicting uterine activity values using measurements from the patient acquired during labor and suitable for implementation in a decision support system, in accordance with an embodiment of the disclosure.

Turning to FIG. 6, alternative embodiments of this disclosure include predicting UA in a future time interval using one or more models that use a peak-over-threshold (POT) function adapted to identify contractions. Specifically, from identifying contractions in the UA time series data, the model may be able to forecast qualities of a future contraction, such as the time of the contraction, the maximum value, and the duration. Each feature may be predicted through a different trained model. Accordingly, even though a plurality of models may be used, the models provide different forecasted measurements, which is in contrast to embodiments utilizing method 200 in which each model provides UA measurements. The predicted feature measurements collectively indicate the future contraction and, as such, can be combined to form a predicted time series. Additionally, in exemplary aspects, the models using the adapted peak-over-threshold approach are trained with data, such as UA times series data, from a reference population.

FIG. 6 provides a flow diagram depicting a method 600 of forecasting a contraction within a future time interval using an adapted peak-over-threshold function. At step 610, a plurality of UA measurements may be acquired for a patient, and a time series may be generated from the UA measurements at step 620. The measurements may be uterine pressure measurements when recorded with an internal monitoring device or may be skin tension recorded through an external device. The measurements may be received and the time series generated (include the pre-processing steps) in the same manner described with respect to method 200.

Figure 7:
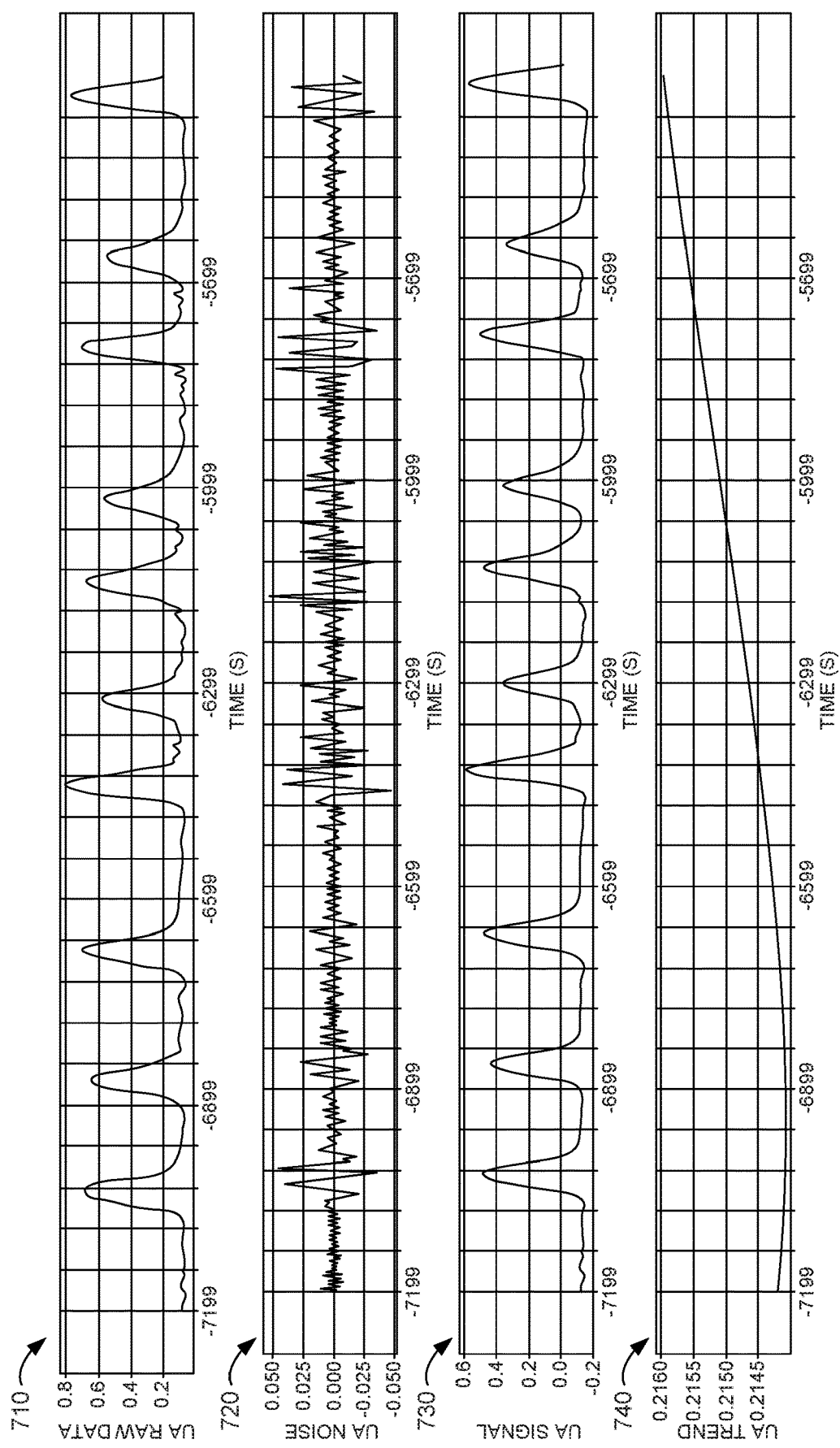
FIG. 7 depicts graphical illustrations of uterine activity sub-signals over time, in accordance with an embodiment of the disclosure.

Additionally, generating the time series may further include filtering. For example, the time series data may be filtered into at least three additional components: noise, signal, and trend. FIG. 7 illustrates a UA time series strip as it is broken down into components, which are also referred to herein as sub-signals. UA time series 710 represents the raw time series data that is traditionally what the healthcare provider is presented when monitoring a patient's UA. UA time series 710 is filtered into different components: UA component 720 representing the noise; UA component 730 representing the UA signal with a mean of 0; and UA component 740 representing the UA trend. The trend shown in UA component 740 is considered a (possibly nonlinear) long-term moving average. The two higher frequency components, UA components 720 and 730, each have a mean of zero such that the areas above and below the curves cancel each other and are equal. The sum of the three components 720, 730, and 740 may be equal to the full time UA series 710.

In some aspects reduced to practice, Ensemble Empirical Mode Decomposition (EEMD) is used to filter the data using the 'Rlibeemd' package in R. Further, in other aspects, the base Empirical Mode Decomposition (EMD) may be used for filtering. In other embodiments, filtering may be performed using wavelet or spectral analysis. When using EEMD or EMD, the time series may be split into more than three components, such as 12 components, and one or more of the components may be summed together to create one of the components illustrated in FIG. 7. For instance, in some aspects, UA component 720 for noise is a sum of five components identified using EMD, and UA component 730 is a sum of two or more components. By using filtering, meaning can be attributed to the components of each UA time series. In some embodiments, the UA component 720 representing noise is not used in the analysis, and the UA component 740 representing trend is effectively the minimum threshold that the UA must exceed to be categorized as a contraction. Further, the UA signal (i.e., UA component 730) may be considered the oscillatory pattern analyzed to detect contractions.

Returning to method 600, a contraction for a future interval may be predicted with a trained model and the UA time series, as shown in step 630. The trained model may utilize an algorithm with a modified peak-over-threshold (POT) function to identify contractions in each data segment. A conventional POT approach finds all values in a time series above a certain threshold based on an assumption that values above that threshold are "extreme" events, and a peak is detected every time the time series rises above the threshold. The peak is considered to end when the time series falls back below the threshold. This standard approach cannot be used to accurately detect contractions, in part, because UA time series data can be sufficiently noisy enough that the standard POT approach would interpret some of the noise to be several weak and quick contractions. Additionally, because monitoring devices also capture the patient "pushing" during labor, the standard approach may interpret the rise in uterine pressure due to the patient's pushing that is not exactly aligned with the actual contraction.

Figure 8:
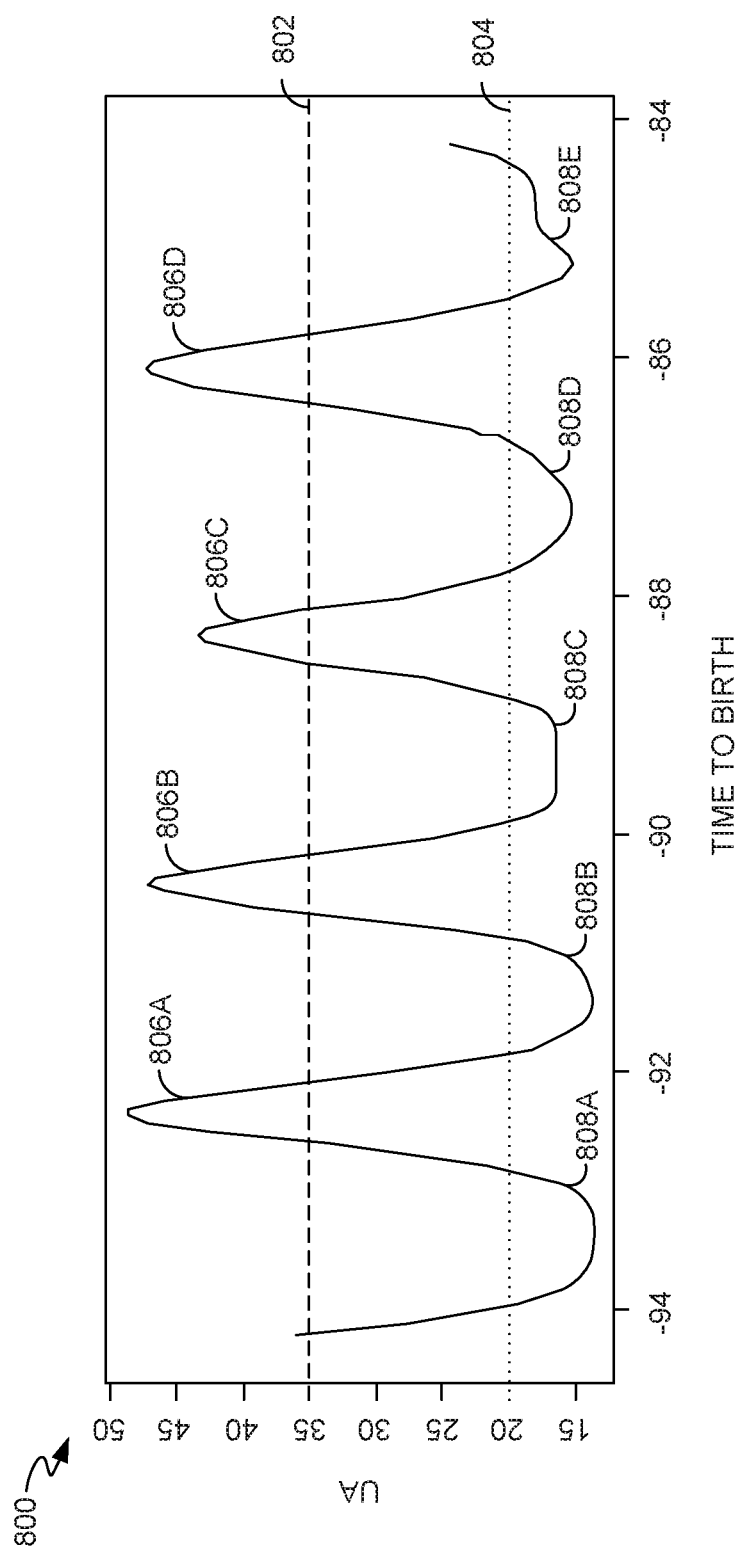
FIG. 8 depicts an example UA monitoring strip with the peak threshold and recovery threshold, in accordance with an embodiment of the disclosure.

Accordingly, embodiments described herein identify a contraction based on a peak threshold H and a recovery threshold L. A peak is detected when the time series rises above H and ends when it falls below H again. However, after a peak ends, a new peak is not registered as a separate contraction unless the time series first falls below L and/or a sufficient duration has passed. In an embodiment, a new contraction is not detected until either the UA values fall below the recovery threshold (L) or 40 seconds has passed since the end of the previous peak (i.e., since the UA values fell below the peak threshold (H)). In alternative embodiments, the threshold duration may be 20 seconds. FIG. 8 illustrates an example UA time series 800 with the red line representing an example peak threshold (H) line 802 and an example recovery threshold (L) line 804. Based on these thresholds, four contractions (e.g., 806A-D) may be identified where the values rise above peak threshold line 802, with each contraction occurring between two recovery periods (e.g., 808A-E) below recovery threshold line 804.

Additionally, the peak threshold and recovery threshold may be updated to capture how UA changes as labor processes. Accordingly, in one aspect, H and L are updated every minute based on the past 10-minutes of data for a particular patient. It is contemplated that the updates may occur more or less frequently and that they may be based on more or less data. Further, in some aspects, when there are two or more possible peaks occurring in quick succession (i.e., before recovery or sufficient time has passed), the highest peak out of the possible peaks is identified as the contraction. In other aspects, multiple possible peaks are split to identify the contraction. For each contraction, the magnitude above H (peak value), the duration of the contraction (time above H in seconds), and the time between the current contraction and the previous one may be recorded.

Using the modified POT approach to identify contractions, one or more models are trained to predict values for a future contraction. In some aspects, the models may be generalized linear models (GLMs), including linear regression models, but it contemplated that additional types of models may be used. Each model may be used to predict values for a different contraction feature. In exemplary aspects, three models are trained to predict, for a future contraction, (1) time between contractions; (2) peak value; and (3) duration of contraction. The contraction may be the next contraction predicted within a future time interval. In some embodiments, the time between contractions is predicted by first forecasting the time using a model trained on a reference population and then using that population-based forecast to create a patient-specific model calibrated based on the specific patient's data for forecasting the time. Using the population-based forecast to create a patient-specific model improves the accuracy for predicting values for time between contractions.

The predictions are based on a certain number of previous contractions identified in the time series data. In some embodiments, the predictions for a future contraction are made using the previous five contractions. In other embodiments, all the contractions in the time series are used. The predicted contraction is the next contraction following the last known contraction, but the process may be repeated using the forecasts for the next contraction to predict additional future contractions. For instance, values for contractions 1-5 may be used to predict contraction 6, and values for contractions for 2-5 and the predicted contraction 6 may be used to predict contraction 7. The predicted values provided by the models may be used to plot the predicted contraction, which may be appended to the known time series data in the monitoring strip and, in some aspects, displayed on a graphic user interface.

In one example reduced to practice, GLMs were trained to predict qualities of the next contraction based on the previous five contractions using the modified peak-over-threshold method. The models were trained using UA data from 34 patients who each had at least 20 minutes of continuous monitoring using an internal device. The models were trained to predict the magnitude (or peak UA value) above the peak threshold, the contraction duration, and the time until the next contraction. A curve was fit to the predicted data for the next contraction, and the process was iterated to obtain a 5-contraction forecast.

Figure 9:
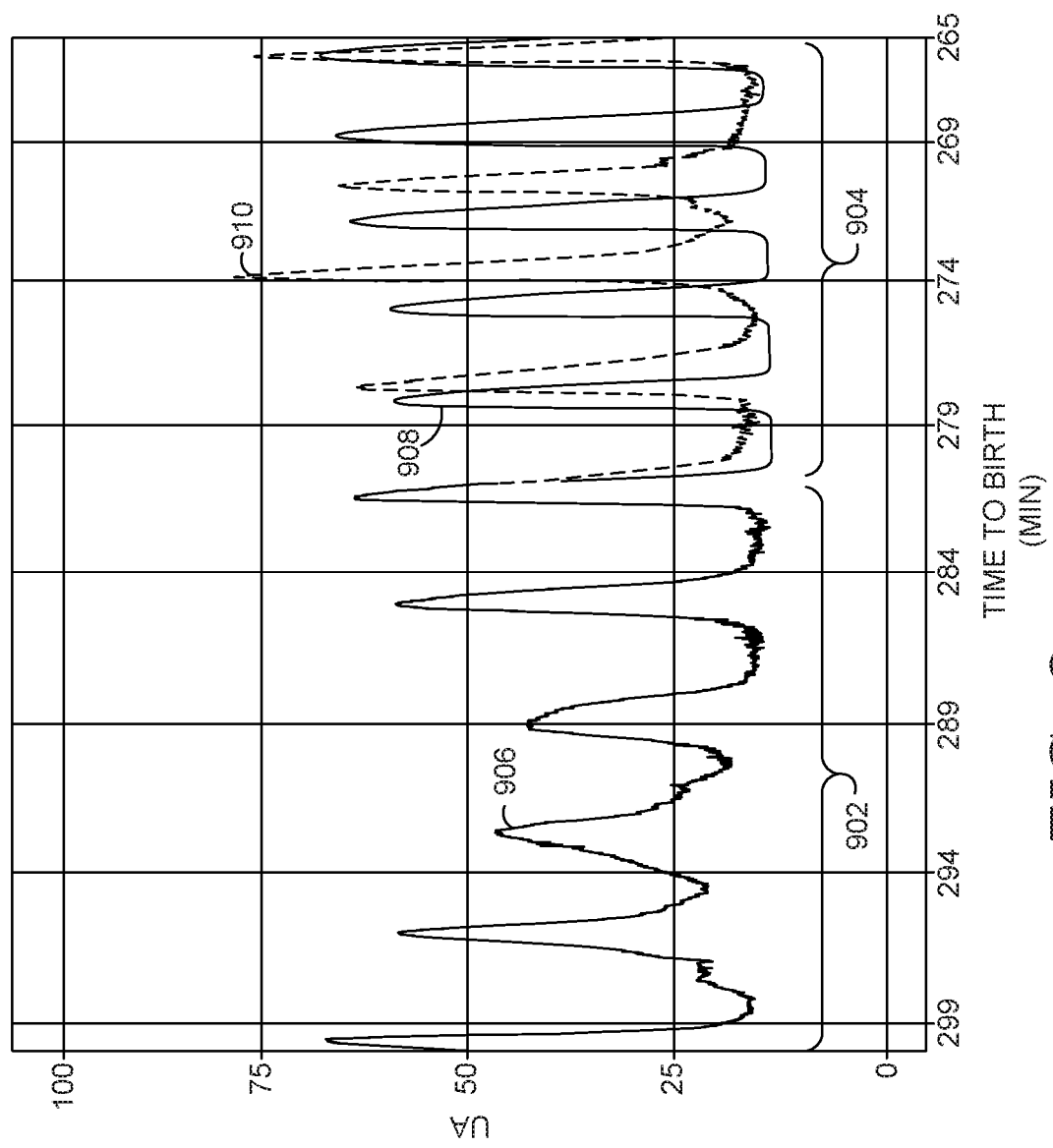
FIG. 9 depicts an example UA monitoring strip with future contractions forecasted using the peak-over-threshold approach, in accordance with an embodiment of the disclosure.

FIG. 9 illustrates an example UA monitoring strip 900 with contractions forecasted by models using the adapted peak-over-threshold approach in accordance with embodiments of the disclosure. Example UA monitory strip 900 depicts a tracing of UA measurements during labor. The UA tracing 906 during time from 902 (300 minutes to 281 minutes prior to birth) represents actual UA values measured for a patient. Forecasted UA tracing 908 (shown as a solid line) in time period 904 (281 minutes to 265 minutes prior to birth) represents UA values predicted using a plurality of models trained to predict contraction feature values based on identifying at least some of the contractions in UA tracing 906 906 using the adapted peak-over threshold approach described herein. Actual UA tracing 910 (shown as a dashed line) in time period 904 illustrates the patient's actual UA measurements during that time period. In some aspects of disclosure, example UA monitoring strip 900 may be presented to a user on a graphic user interface.

Figure 10A:
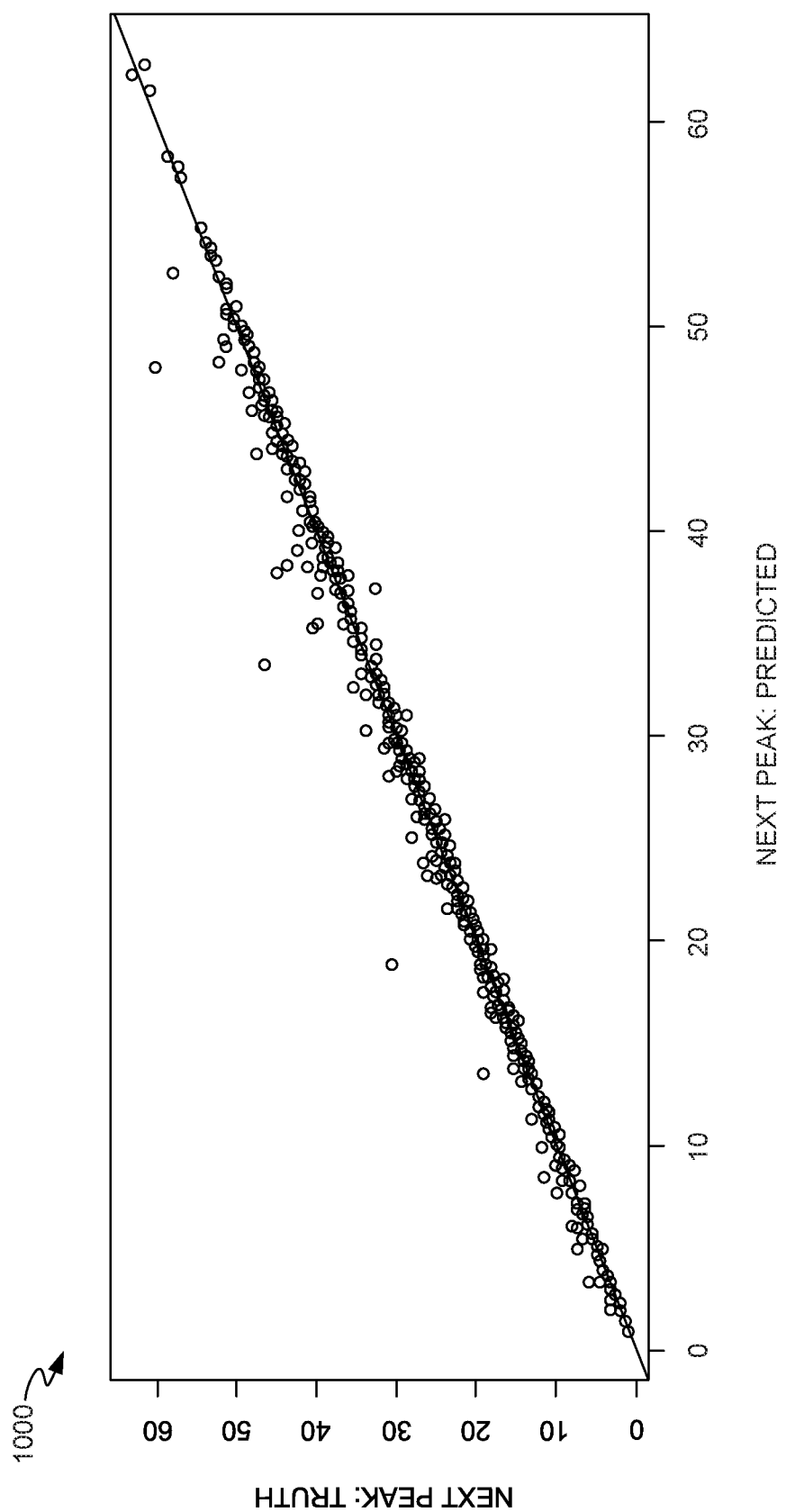
FIGS. 10A-10C depict graphical illustrations of the accuracy of forecasted values of the next peak, duration, and lag, respectively, in an example embodiment reduced to practice.
Figure 10B:
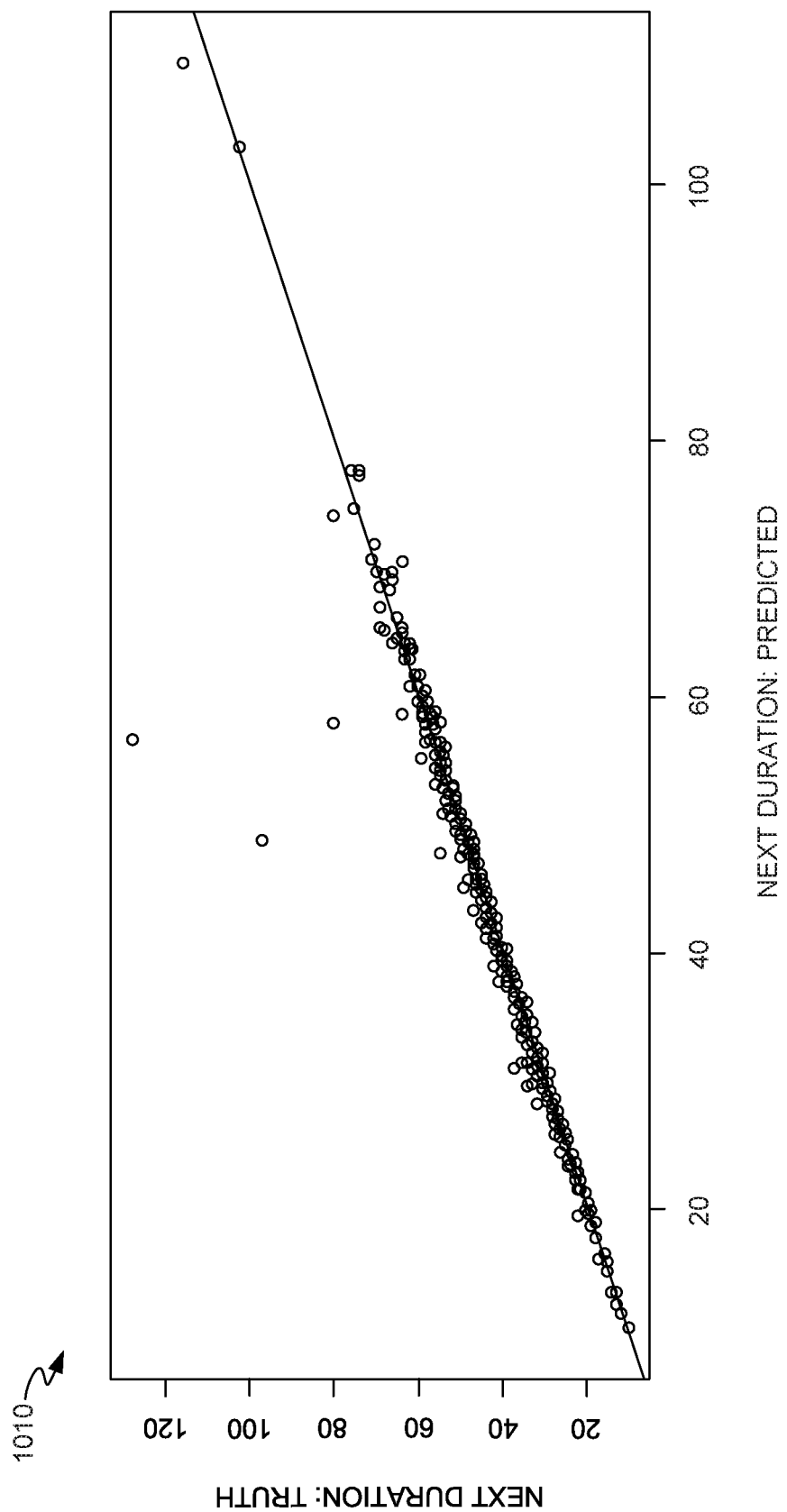
Figure 10C:
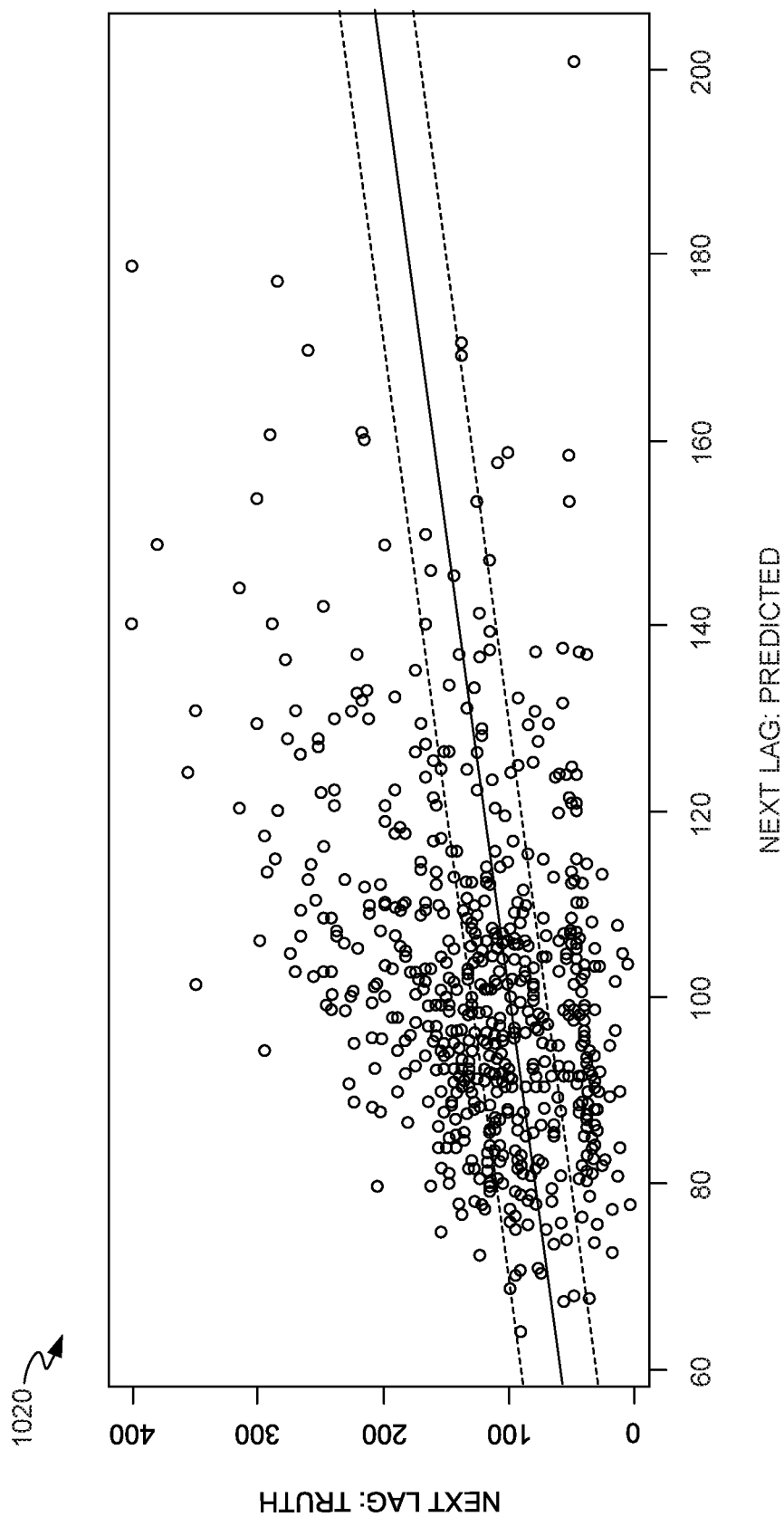

FIGS. 10A, 10B, and 10C depict graphic illustrations indicating the accuracy of an embodiment reduced to practice. Specifically, FIG. 10A depicts a graph 1000 showing the relationship between peak values predicted by the forecast model and the actual peak values; FIG. 10B depicts graph 1010 showing the relationship between duration values predicted by the forecast model and the actual duration values; and FIG. 10C depicts graph 1020 showing the relationship between time between contractions (lag) predicted by the forecast model and the actual times between contractions. The dashed lines in graph 1020 in FIG. 10C represent a 30-second window.

Based on the forecasted contraction(s), a response action may be initiated, as shown at step 640 of FIG. 6. One such response action may be a recommendation or notification that is emitted or otherwise communicated to a caregiver responsible for the patient's care, such as an obstetrician. For instance, when the forecasted contraction indicates a contraction with a peak value above a threshold and/or within a threshold duration, a notification of the forecasted contraction may be generated and communicated via a bedside alarm, user/clinician interface (such as interface 142 described in FIG. 1A), or may be communicated to a smartphone or personal computing device of a caregiver. The notification may illustrate the forecasted contraction on a UA monitoring strip and/or may indicate that the next contraction is forested to be a strong contraction. Similarly, notifications may be provided when the contraction is predicted within a future time frame to indicate that a next contraction may be expected within the near future. Additionally, some embodiments of step 640 may comprise storing the result of the forecasted contraction(s) in an EHR associated with the patient and further may include providing the patient's EHR (or facilitating access to the EHR) in the notification.

In addition to or alternatively of the notification, a set of one or more actions relating to therapeutic responses may be initiated. For example, as described herein, the forecasted contraction may indicate that the contractions should be monitored by a care giver, such as an obstetrician, and based on that determination, may recommend monitoring and/or admittance to the hospital. In some embodiments, a determination that the contractions are forecasted within a sufficient frequency may initiate a recommendation for monitoring by a caregiver. For instance, when contractions first begin, the expecting mother may monitor the contractions at home to determine when to go to the hospital for delivery. Additionally, some embodiments recommend actions based on determinations that labor is not progressing in an expected way based on the forecasts. A recommendation may be provided in conjunction with a notification of the forecasted contractions and/or may be provided via a user/clinician interface, such as interface 142, described in connection with FIG. 1A.

Yet another action that may be initiated comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan due to the expected upcoming contractions. A further action that may be initiated comprises scheduling healthcare resources for the patient. For example in one embodiment, it may be determined based on forecasted contractions that the patient has reached a threshold contraction duration and/or strength that the patient, and additional resources, such as staff, may be scheduled to monitor and treat the patient in labor. In one embodiment, this action comprises modifying or updating a resource/scheduling electronic record in a resource/scheduling system.

Many different arrangements of the various components depicted, as well as components not shown, are possible without departing from the spirit and scope of the present disclosure. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Non-transitory computer-readable media having computer-executable instructions embodied thereon that when executed, provide a method for a decision support system for patients in labor using uterine activity forecasts, the method comprising:
   receiving a plurality of uterine activity (UA) measurements for a patient in labor, the plurality of UA measurements being acquired over a time span and corresponding to a set of contractions experienced by the patient;
   constructing a time series from the plurality of UA measurements;
   based on the time series of UA measurements corresponding to the set of contractions, forecasting one or more future contractions to occur within a future time interval for the patient using a plurality of models, wherein each model within the plurality of models is trained to predict a UA feature value for each future contraction within the one or more future contractions, wherein the plurality of models comprises at least:
      a first reference model trained with UA data from a reference population to predict at least a first value for a first UA feature of future contractions using the time series of UA measurements; and
      a first patient-specific model trained with UA measurements of the patient to predict at least a second value for the first UA feature of future contractions using a time series of UA measurements of the patient including the at least first value of the first UA feature; and
   based on the one or more future contractions that are forecasted, initiating a response action for the patient.

2. The media of claim 1, wherein the plurality of models includes a third model trained to predict a length of time between contractions, wherein the third model comprises a reference model trained using UA data from a reference population, and wherein the method further comprises using a fourth model that is trained with UA measurements of the patient to predict time between contractions using the one or more predictions of a length of time between contractions from the third model.

3. The media of claim 1, wherein each model within the plurality of models comprises a linear regression model.

4. The media of claim 1, wherein the UA feature values predicted by the plurality of models are combined to forecast the one or more future contractions.

5. The media of claim 1, wherein the plurality of models are trained to identify contractions in the time series of the patient.

6. The media of claim 5, wherein contractions are identified when a UA value exceeds a peak threshold and either when UA values fall below a recovery threshold that is different than the peak threshold or when a predetermined duration has passed.

7. The media of claim 1, wherein the response action comprises one or more of:
   automatically generating and communicating an electronic notification to a caregiver of the patient;
   generating and providing a recommendation for increased monitoring of the patient;
   modifying computer code executed in a healthcare software program for treating the patient; or
   scheduling healthcare resources for the patient.

8. The media of claim 1, wherein the plurality of models further comprises a third model trained to predict the duration of the future contraction.

9. The media of claim 8, wherein the plurality of models further comprises a fourth model trained to predict the peak value of the future contraction.

10. The media of claim 9, wherein the plurality of models further comprises a fifth model trained to predict a length of time between contractions.

11. The media of claim 10, wherein the fifth model is trained to predict a length of time between an end of a first future contraction and a start of a second future contraction.

12. The media of claim 1, wherein the at least first value of the first UA feature includes a length of time between contractions.

13. The media of claim 1, wherein the at least first value of the first UA feature includes a peak value of a contraction.

14. A system forecasting uterine activity within a future time interval, the system comprising:
   one or more processors;
   memory storing computer-usable instructions that, when executed by the one or more processors, implement a method comprising:
      receiving a plurality of uterine activity (UA) measurements for a patient in labor, the plurality of UA measurements being acquired over a time span and corresponding to a set of contractions experienced by the patient;
      constructing a time series from the plurality of UA measurements;

based on the time series of UA measurements corresponding to the set of contractions, forecasting one or more future contractions to occur within a future time interval for the patient using a plurality of trained models, wherein the plurality of trained models comprises at least:
- a first reference model trained with UA data from a reference population to predict at least a first value for a first UA feature of future contractions using the time series of UA measurements; and,
- a first patient-specific model trained with UA measurements of the patient to predict at least a second value for the first UA feature of future contractions using a time series of UA measurements of the patient including the at least first value of the first UA feature; and based on the one or more future contractions that are forecasted, initiating a response action.

15. The system of claim 14, wherein when the plurality of trained models are trained to identify contractions in the time series.

16. The system of claim 15, wherein contractions are identified when a UA value exceeds a peak threshold and either when UA values fall below a recovery threshold or when a predetermined duration has passed.

17. The system of claim 16, wherein the predetermined duration is 40 seconds.

18. The system of claim 16, wherein the recovery threshold and the peak threshold are updated periodically based on additional UA measurements received for the patient.

19. The system of claim 14, wherein the one or more future contractions that are forecasted comprise five future contractions.

20. The system of claim 14, wherein the method further comprises determining fetal distress from the one or more future contractions that are forecasted and wherein the response action comprises automatically generating and communicating an electronic notification to a caregiver of the patient.

21. A computerized method for forecasting uterine activity within a future time interval, the method comprising:
receiving a plurality of uterine activity (UA) measurements for a patient in labor, the plurality of UA measurements being acquired over a time span and corresponding to a set of contractions experienced by the patient;
constructing a time series from the plurality of UA measurements;
based on the time series of UA measurements corresponding to the set of contractions, forecasting one or more future contractions to occur within a future time interval for the patient using a plurality of models, wherein each model within the plurality of models is trained to predict a UA feature for the future time interval using an adapted peak-over-threshold approach for identifying contractions in the time series, wherein the plurality of models comprises at least:
- a first reference model trained with UA data from a reference population to predict at least a first value for a first UA feature duration of a future contraction using the time series of UA measurements, and
- a first patient-specific model trained with UA measurements of the patient to predict at least a second value for the first UA feature of magnitude of the future contractions using a time series of UA measurements of the patient including the at least first value of the first UA feature; and based on the one or more future contractions that are forecasted, initiating a response action.

22. The method of claim 21, wherein the adapted peak-over-threshold approach for identifying contractions comprises identifying a contraction when a UA value exceeds a peak threshold and either when UA values fall below a recovery threshold or when a predetermined duration has passed.

* * * * *